US007927632B2

(12) United States Patent
Yoon et al.

(10) Patent No.: US 7,927,632 B2
(45) Date of Patent: Apr. 19, 2011

(54) COMPOSITIONS FOR STERILIZING SPORES OF SPORE-FORMING MICROORGANISMS COMPRISING THE EXTRACTS OF TORILIDIS FRUCTUS

(75) Inventors: Hee Nam Yoon, Seoul (KR); Jun Bong Choi, Seoul (KR); Won Il Cho, Seoul (KR); Yu Ryang Pyun, Seoul (KR); Seok Cheol Cho, Seoul (KR); Moo Chang Kook, Seoul (KR); Byoung Gon Lee, Seoul (KR)

(73) Assignee: CJ Cheiljedang Corporation (KR)

( * ) Notice: Subject to any disclaimer, the term of this patent is extended or adjusted under 35 U.S.C. 154(b) by 281 days.

(21) Appl. No.: 11/794,608

(22) PCT Filed: Jan. 4, 2006

(86) PCT No.: PCT/KR2006/000028
§ 371 (c)(1),
(2), (4) Date: Jul. 3, 2007

(87) PCT Pub. No.: WO2006/073266
PCT Pub. Date: Jul. 13, 2006

(65) Prior Publication Data
US 2009/0022820 A1 Jan. 22, 2009

(30) Foreign Application Priority Data

Jan. 4, 2005 (KR) .......................... 10-2005-0000600

(51) Int. Cl.
*A61K 36/00* (2006.01)
*C12N 1/20* (2006.01)
(52) U.S. Cl. ................. 424/725; 425/252.31; 425/252.7
(58) Field of Classification Search .................. None
See application file for complete search history.

(56) References Cited

U.S. PATENT DOCUMENTS 6,680,076 B2 * 1/2004 Nam .............................. 424/725

FOREIGN PATENT DOCUMENTS

| JP | 04334319 A | * | 11/1992 |
| JP | 08283167 A | * | 10/1996 |
| JP | 2000302673 A | * | 10/2000 |
| KR | 100172136 | | 10/1998 |
| KR | 10-2000-0044985 | | 5/2000 |
| KR | 10-2001-0014909 | | 2/2001 |
| KR | 10-2002-0068021 | | 8/2002 |
| KR | 10-2005-0005196 | | 1/2005 |

OTHER PUBLICATIONS

Jain et al. "Anti-inflammatory effects of Erythromycin and Tetracycline on Propionibacterium acnes induced production of chemotactic factors and reactive oxygen species by human neutrophils". Dermatology Online Journal, vol. 8, No. 2 (2002), Article 2. Retrieved from: <http://dermatology.cdlib.org/DOJvol8num2/original/antibiotics2/jain.html>.*
Esteban et al. "Granulomatous infection due to Propionibacterium acnes mimicking malignant disease" European Journal of Clinical Microbiology & Infectious Diseases, vol. 13, No. 12 (Dec. 1994) 1084-1086.*
Notification of the First Office Action from the Patent Office of the People's Republic of China mailed Jun. 5, 2009 in Application No. 200680001789.6.
Chinese Patent Application No. 01127083 entitled "Application of Cnidiadin in Agriculture".
English Translation of Abstract of *Primary Study on the Inhibition Effect of Crude Extract of Torilidis Fructus on Phytopathogenic Fungi*, Tian Xiuling et al., Abstract in Book of the Seventh Academic Congress of Chinese Society of Plant Pathology, p. 163, (2002).
Huang, Database WPI Section Ch, Week 199741, Thomson Scientific London, GB; AN 1997-436111, XP002589227 & CN 1 116 047, Feb. 7, 1996.
Xie, Database WPI Section Ch, Week 200526, Thomson Scientific London, GB; AN 2005-242919, XP002589228 & CN 1 554 232, Dec. 15, 2004.
Yang, Database WPI Section Ch, Week 200477, Thomson Scientific London, GB; AN 2004-776354, XP002589226 & CN 1 517 116, Aug. 4, 2004.
Extended European Search Report for European Application No. 06700341.8 dated Jul. 6, 2010.

* cited by examiner

*Primary Examiner* — Amy L Clark
(74) *Attorney, Agent, or Firm* — Hunton & Williams LLP (57) ABSTRACT

Disclosed are a composition comprising an organic acid extract of Torilidis Fructus, which has a sterilization effect on spores of spore-forming microorganisms including fungi and bacteria, and a method of sterilizing spores and vegetative cells using the composition.

4 Claims, 8 Drawing Sheets

Fig. 1

Sterilization effects of natural antimicrobial materials

| Natural antimicrobial materials | Bacillus subtilis spores (CFU/ml) | Inactivation (%) |
|---|---|---|
| No addition (Saline) | $5.23 \times 10^4$ | |
| Coriander, *Coriandum sativum* | $1.36 \times 10^4$ | 74.00 |
| *Portulace oleracea* | $3.67 \times 10^5$ | 0.00 |
| *Torilidis fructus* | $4.44 \times 10^1$ | 99.92 |
| *Arctii semen* | $1.57 \times 10^4$ | 69.98 |
| *Gardeniae fructus* | $8.33 \times 10^3$ | 84.07 |

Conc. of the ethanol extract of Torilidis Fructus (%)

| Conc. of the ethanol extract of Torilidis Fructus (%) | Bacillus subtilis spores (CFU/ml) | Inactivation (%) |
|---|---|---|
| No addition (Saline) | $2.97 \times 10^4$ | |
| 1.00 % | $9.38 \times 10^0$ | 99.97 |
| 0.50 % | $1.04 \times 10^1$ | 99.96 |
| 0.10 % | $6.21 \times 10^2$ | 97.91 |
| 0.05 % | $3.26 \times 10^4$ | 0.00 |
| 0.01 % | $2.48 \times 10^4$ | 16.50 |

Fig. 4

Treatment time with the ethanol extract of Torilidis Fructus

| Treatment time with the ethanol extract of Torilidis Fructus (h) | Bacillus subtilis spores (CFU/ml) | Inactivation (%) |
|---|---|---|
| No addition (Saline) | $1.06 \times 10^5$ | |
| 0 | $1.84 \times 10^4$ | 82.64 |
| 0.5 | $1.29 \times 10^3$ | 98.78 |
| 1 | $8.38 \times 10^1$ | 99.92 |
| 2 | $1.08 \times 10^2$ | 99.90 |
| 3 | $6.69 \times 10^1$ | 99.94 |
| 6 | $2.71 \times 10^1$ | 99.97 |

Control I
(*B. subtilis* spore suspension, after 5 hrs)

Control II
(*B. subtilis* spore suspension mixed with nutrient medium (TSB), after 5 hrs)

Treatment group with the hexane extract from the ethanol extract of Torilidis Fructus
(*B. subtilis* spore suspension, after 5 hrs)

Treatment group with the water extract from the ethanol extract of Torilidis Fructus
(*B. subtilis* spore suspension, after 5 hrs)

Fig.8

Control
(*B. subtilis* spore suspension, after 5 hrs)

Treatment group with the ethanol extract
of Torilidis Fructus
(*B. subtilis* spore suspension, after 5 hrs)

Treatment group with the hexane extract
from the ethanol extract of Torilidis
Fructus
(*B. subtilis* spore suspension, after 5 hrs)

Treatment group with the water extract
from the ethanol extract of Torilidis
Fructus
(*B. subtilis* spore suspension, after 5 hrs)

COMPOSITIONS FOR STERILIZING SPORES OF SPORE-FORMING MICROORGANISMS COMPRISING THE EXTRACTS OF TORILIDIS FRUCTUS

CROSS-REFERENCE TO RELATED APPLICATIONS

This application is the National Stage of International Application No. PCT/KR2006/000028, filed Jan. 5, 2006, which claims the benefit of Korean Patent Application No. 10-2005-0000600, filed Jan. 4, 2005, the disclosures of each of which are herein incorporated by reference in their entireties.

TECHNICAL FIELD

The present invention relates to a composition for sterilizing spores of spore-forming microorganisms, comprising an extract of Torilidis Fructus, and a sterilization method using the composition.

BACKGROUND ART

Spore-forming microorganisms belonging to aerobic *Bacillus* species and obligate anaerobic *Clostridium* species, which are naturally occurring in agricultural raw materials harvested from the soil, such as vegetables and spices, form highly heat-resistant endospores, and thus serve as direct or indirect causes of deterioration of the quality of processed food products and threaten food hygiene.

The spore core is maintained in a dehydrated and dried state, and is surrounded by a peptidoglycan layer called the cortex. The cortex is encased in the coat layer composed largely of proteins. Due to the specialized structure and biochemical properties, spores are highly resistant to heat, chemical reagents such as antimicrobial substances or antibiotics, lysozymes, physical impacts, UV radiation, high pressure, high voltage pulse electric fields, and the like. Spores can remain dormant for long periods of time to survive in unfavorable growth environments. Thus, sterilization conditions for spores must be primarily considered to ensure the microbial safety of processed food products.

In addition, spore-forming microorganisms, which are problematic because they are naturally occurring in soil-derived food raw materials, such as vegetables and spices, are significant risk factors in the sterilization of retort products charged into various types of containers, such as cans, pouches and trays. That is, spore-forming microorganisms are secondary contaminants resulting from the generation of cold points, at which sufficient heat treatment of over Fo 4 is not achieved, and problems with packaging materials, such as pin holes, and thus are major sterilization targets.

It is therefore important to research and develop germination inhibition and sterilization methods of spore-forming microorganisms in order to ensure the hygiene and shelf life of processed food products.

Since pathogens not forming spores have weak resistance to heat and low resistance to chemical treatment, they are sufficiently inhibited in growth or killed by heat treatment at less than 100° C. or by treatment with commercialized antimicrobial agents, such as organic acids, alcohol and bacteriocine. In contrast, spores are not easily killed due to their structural, chemical and ecological properties. Thus, heat-resistant spores are typically killed using a retort sterilization method based on heating at a high temperature of 121° C. under a high pressure of 1-1.5 Kg/cm$^2$ for a period ranging from a few minutes to several tens of minutes. However, such high temperature treatment significantly damages sensory qualities including taste, appearance and texture, and destroys a lot of nutrients, thereby impeding the development of high-quality processed food products. Another commercial sterilization method involves indirect sterilization, which is based on inducing germination of spores at a mild temperature of 65° C. for 5 to 6 hours to convert spores into vegetative cells and performing sterilization. This method has an advantage of allowing sterilization of heat-resistant spores at temperatures lower than 100° C. without quality reduction, but has some drawbacks including the fact that it is time-consuming when applied to industrial production and entails a high risk of microbial contamination in summer. Also, methods of inhibiting spore germination are used, which employ sodium lactate, lysolecithin, poly fatty acid ester, L-phenylalanine, essential oils, glycine, L-serine, and the like. However, since these methods using food additives have only inhibitory effects on spore germination and no spore-killing effect, potential risk factors remain.

In addition, studies have been performed for various antimicrobial compositions.

According to Alkhayat, Huhtanen, Ueda, et al., hot water and ethanol extracts of spices, such as clove, mace, white and black pepper, laurel, and nutmeg, have growth inhibitory effects on spores of *Bacillus botulinus* types A and B at a minimal inhibition concentration (MIC) of 125 μg/ml. According to Hara et al., tea extracts, such as tannine, polyphenol, theaflavin and catechin, are effective in inhibiting the germination of spores. Also, caffeic acid and protamine, which is a highly-basic protein (peptide) binding to DNA in the nuclei of the sperm of fish, are effective in killing spores and inhibiting spore germination. Protamine kills vegetative cells of *Bacillus* species by damaging the cell wall and the plasma membrane, and has growth inhibitory effects on spores of *Bacillus* species through the inhibition of DNA, RNA and protein synthesis and respiration inhibition in the ATP level. Also, the spore death may be greatly stimulated by protamine's cooperative action with heat. In addition, other natural antimicrobial materials, which are known to have an inhibitory effect on spore germination and a sterilization effect on spores, include the following: polylysine, which has a growth inhibitory effect by serving as a surfactant affecting the spore structure; peptides and proteins consisting of amino acids, such as bacteriocine, nisin and pediocines, which do not directly affect dormant spores, but affects the core of germinating spores by penetrating the thin membrane of spores at the early swelling stage of spore germination, thereby inhibiting propagation; and ethanol, which has a growth inhibitory effect during spore germination or sporulation. However, most antimicrobial agents against spores have a growth inhibitory action rather than a direct sterilization effect against dormant spores, or display only growth inhibitory action during spore germination or sporulation. Also, substances having direct sterilization effects display an unsatisfactory spore-killing effect of about 10$^1$.

A review of related domestic and foreign literature yields the following. Korean Pat. Application No. 1992-18019 discloses a composition having an inhibitory effect on spore germination, comprising an extract from a mixture of defatted starch of a plant species belonging to the genus *Ricinius* and roots of another plant species belonging to the genus *Coptis*, and states that berberine is a key substance in the inhibition of spore germination. Korean Pat. Application No. 1996-7000557 discloses a method and a composition for killing or inhibiting the growth of yeast or spore-forming microorganisms by contacting the microorganisms, in the presence of a peroxide and chloride or bromide, with a haloperoxidase and at least one antimicrobial activity enhancing agent. This patent describes that the antimicrobial activity enhancing agent includes certain alpha-amino acids, and are preferably compounds having a structure which contains hydrogen, an unsubstituted or hydroxyl- or amino-substituted, straight or branched chain alkyl group having from 1 to 6 carbon atoms, or an unsubstituted or hydroxyl- or amino-substituted arylalky group having from 7 to 12 carbon atoms. This patent also describes that the antimicrobial activity enhancing agents include alpha-amino acids selected from the group consisting of glycine and l- or d-enantiomers of alanine, valine, leucine, isoleucine, serine, threonine, lysine, phenylalanine and tyrosine, and alkyl esters thereof. Japanese Pat. Application No. 1995-72164 discloses a diglycerine fatty acid monoester composition for inhibiting the germination and propagation of heat-resistant spores which cause some problems in beverage processing, comprising fatty acids, such as lauric acid, myristic acid and palmitic acid, and monoester. Japanese Pat. Application No. 1993-301163 discloses a method of inducing inhibition of spore germination using a composition comprising fatty acids including glycerine monostearic acid ester and isolecithin. The aforementioned inventions mainly aim to inhibit the growth of spores, and most antimicrobial materials described in these inventions cab be considered synthetic food additives rather than natural antimicrobial materials.

Based on this background, the intensive and through research into the development of natural antimicrobial agents having an effect of completely sterilizing spores with no side effects resulted in the finding that among one hundred edible plant materials including herbal spices, Chinese herbal medicines, tropical fruits and vegetables, an extract of Torilidis Fructus has a very strong sterilization effect on spores of *Bacillus subtilis*, thereby leading to the present invention.

DISCLOSURE OF THE INVENTION

It is therefore an object of the present invention to provide a composition for sterilizing spores of spore-forming microorganisms, comprising an organic solvent extract of Torilidis Fructus.

It is another object of the present invention to provide a method of sterilizing spores of spore-forming microorganisms, which is based on treating the spores with the composition.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

In one aspect, the present invention relates to a composition for sterilizing spores of spore-forming microorganisms, comprising an organic solvent extract of Torilidis Fructus.

As used herein, the term "extract", which is an active ingredient isolated from plants, is intended to indicate a substance that has antimicrobial and sterilization activity against spores and vegetative cells of spore-forming microorganisms. The extract is prepared by an extraction process using an organic solvent such as alcohol. The extract includes an organic solvent extract, dried powder thereof, and all formulations prepared using the same. The extract of the present invention is an extract of Torilidis Fructus.

In the present invention, "Torilidis Fructus" means a dried fruit of plants belonging to the Family Umbelliferae, *Torilis japonica* Decandolle and *Cnidium monnieri* (L.) Cussion, and includes all wild-type, hybrid and mutant types of Torilidis Fructus.

Torilidis Fructus has been used in Chinese herbal medicine for a long time, for treating various skin conditions including itching, skin wounds, eczema and furuncles. Also, Torilidis Fructus has been known to have some therapeutic effects on trichomonal vaginitis. In addition to the use in Chinese herbal medicine for treating skin disorders, Torilidis Fructus has been recently utilized as an insecticidal agent. Nurayama et al. reported that Torilidis Fructus has astringent and anti-inflammatory effects (Shokubutsu Kenkyn Zasshi, 3, 181, 1926). Itokawa et al. reported the sedative effect of Torilidis Fructus, effected by the action of sesquiterpene (Shoyakugaku Zasshi, 37, 223, 1983). Shindo et al. reported that an extract of Torilidis Fructus has a complement-inhibitory effect of more than 80% (Wakakanyaku Symposium, 16, 76, 1983). Korean Pat. Application No. 2000-0006823 describes a composition for alleviating skin itching comprising an extract of Torilidis Fructus. Korean Pat. Application No. 1995-013750 discloses anti-rheumatoid, anti-inflammatory and analgesic drugs.

Major components of Torilidis Fructus include l-camphene, bergapten, β-eudesmol, columbianetin, archangelicin, edultin, isopimpinelline and anthotoxol. Torilidis Fructus also contains about 1.3% essential oils.

Although Torilidis Fructus has been traditionally used in Chinese herbal medicine as a therapeutic agent for skin disorders, its sterilization effect on spores has not been known. The Torilidis Fructus extract of the present invention is characterized by sterilizing vegetative cells of the aforementioned spore-forming microorganisms as well as spores that can survive in harsh environments such as high temperature, acids, bases, dryness, chemical reagents and radiation. The present inventors analyzed the sterilization effects of one hundred plant ethanol extracts on spores of *Bacillus subtilis* by measuring OD values and total bacterial cell number. As a result, an extract of Torilidis Fructus was found to have an excellent sterilization effect of reducing spores of *Bacillus subtilis* by $10^3$-$10^4$ CFU/ml (99.9-99.99% inactivation). This sterilization effect amounts to more than 100 times the conventional spore-killing effect of about $10^1$. In addition, the Torilidis Fructus extract of the present invention is characterized by inducing spore death through the induction of fracture damage to the coat layer of spores, rather than simply inhibiting the germination of spores of heat-resistant Bacillus species.

The term, "spore-forming microorganisms", as used herein, means all microorganisms that form spores, and includes fungi and bacteria. The Torilidis Fructus extract of the present invention has an excellent sterilization effect on vegetative cells and spores of all spore-forming microorganisms, and particularly, has an excellent sterilization effect on vegetative cells and spores of spore-forming bacteria. Examples of spore-forming bacteria include bacteria of the genus Bacillus, which include Bacillus natto, Bacillus subtilis, Bacillus megaterium, Bacillus stearothermopjilus, and Bacillus coagulans; and bacteria of the genus Clostridium, which include Clostridium butylicum, Clostridium acetobutylicum, Clostridium botulinum, Clostridium sporogenes, and Clostridium welchii.

In the present invention, Torilidis Fructus is extracted with an organic solvent. The resulting extraction solution may be used immediately, but may be preferably used after being filtered and dried.

The extract of the present invention is prepared through a process including grinding Torilidis Fructus, extracting it with a solvent, filtering the extract and drying the filtrate.

Torilidis Fructus may be extracted with an organic solvent, such as methanol, ethanol, isopropanol, butanol, ethylene, acetone, ether, chloroform, ethylacetate, N,N-dimethylformamide (DMF), or dimethylsulfoxide (DMSO), under a condition in which effective ingredients of the herbal medicine are not destroyed, or this destruction is minimized, at room temperature or elevated temperature. Preferably, the extraction is carried out at 20° C. to 30° C. for about 12 hours to about 48 hours. Since the degree of extraction and loss of effective ingredients of the herbal medicine may vary according to the organic acids used, a suitable organic acid should be selected. Filtration is a step for removing suspending solid particles from the extract. The removal of solid particles may be achieved by passing through cotton, nylon, or the like, freezing filtration, or centrifugation, but the present invention is not limited to those methods. The drying of the filtrate may be achieved by freeze drying, vacuum drying, hot air drying, spray drying, pressure drying, foam-mat drying, high frequency drying, and infrared ray drying, but the present invention is not limited to those methods. The process may further include a step of concentrating the filtrate before the drying step. If desired, the process may further include a step of grinding the final dried extract.

In a detailed embodiment of the present invention, Torilidis Fructus was extracted with ethanol at 25° C. for 24 hours with stirring, and passed through a Whatman paper to remove water-insoluble substances. The filtrate was concentrated in a vacuum at 44° C. and freeze-dried to give an extract of Torilidis Fructus.

The organic solvent extract of Torilidis Fructus, prepared according to the process, contains bornyl acetate and geranyl acetate.

An ethanol extract of Torilidis Fructus is extracted with hexane, and the resulting hexane extract is assessed for effective ingredients having antimicrobial activity responsible for spore sterilization. As a result, among ingredients including pinene, cymene, limonene, osthol, camphene, bornyl acetate and geranyl acetate, the bornyl acetate and geranyl acetate ingredients, which have both hydrophobic and hydrophilic groups and thus can serve as surfactants, exhibit major sterilization effects against vegetative cells and spores of spore-forming microorganisms.

The two major effective ingredients, bornyl acetate and geranyl acetate, kill spores by directly damaging the surface structure of the outermost coat layer of spores, which is composed largely of proteins. These ingredients have both hydrophilic hydroxyl (OH), ester (RCOOR) and carboxyl (RCOOH) groups and a hydrophobic methyl ($CH_3$) group. Due to this surfactant-like structure, one molecule of these ingredients binds to both hydrophilic and hydrophobic groups of the cell wall and cell membrane of vegetative cells, leading to modification of and damage to vegetative cells, and also binds to both hydrophilic and hydrophobic groups of the coat layer of spores, leading to modification of protein components, thereby causing fracture damage to the spore coat, thereby eventually killing vegetative cells and spores.

In addition, the organic solvent extract of Torilidis Fructus, prepared according to the method, includes alanine, mannitol and xylitol.

When the water extract from the ethanol extract of Torilidis Fructus is added to a spore suspension, the early events of spore germination are triggered by germination stimulators. The germination stimulators contained in the ethanol extract of Torilidis Fructus are alanine, mannitol and xylitol.

Germination stimulators known so far include amino acids having a hydrophobic alkyl group, such as L-alanine, L-aminobutyrate, aminoisobutyrate, L-valine, L-isoleucine, L-cystein and L-glutamine, caramelized sugars, and L-asparagine, which induces germination by a mechanism different from that of L-alanine. In addition, aldoses, such as glucose, mannose, xylose, rhamnose and sucrose, and a deoxy derivative of aldoses, 2-deoxyglucose, and lactone derivatives of aldoses, glucono-1,4-lactone and galactono-1,4-lactone, mannitol, sorbitol, xylitol, and the like, are known as carbohydrate-based germination inducers. In addition, sodium, potassium and phosphate ions are know to greatly stimulate the germination triggered by L-alanine, but they do not act as germinators by themselves. GC-MS analysis revealed that the ethanol extract of Torilidis Fructus according to the present invention contains large quantities of alanine, mannitol and xylitol.

Spore germination is a process including Stage 1, in which germinators binds to spore receptors; Stage 2, in which early events of germination are triggered; Stage 3, in which water penetrates into the dehydrated spore core, resulting in the loss of heat resistance, and dipicolinic acid and calcium ions are released from the spore core; Stage 4, in which this core rehydration triggers the hydrolysis of the spore cortex; Stage 5 in which, as the spore core expands, fractures are formed in the central region of the core; and Stage 6, in which the core cell is released, completing the germination process. Scanning electron microscopic observations resulted in the finding that the spore germination stimulators contained in the water extract from the ethanol extract of Torilidis Fructus act at Stage 1 and Stage 2 in spore germination. Also, since the water extract from the ethanol extract of Torilidis Fructus does not contain specific nutrients other than the germination stimulators, it does not lead to cortex hydrolysis at Stage 4, but is considered merely to cause partial damage to the spore coat, that is, to form channels by causing fractures allowing antimicrobial ingredients of the hexane extract to diffuse into the spore coat. That is, alanine, mannitol and xylitol have only a germination stimulating action leading to changes in the spore coat, and do not affect the stage involving spore DNA release from the spore core and conversion of the spore to a vegetative cell.

The organic solvent extract of Torilidis Fructus according to the present invention exhibits a synergistic effect on spore sterilization, which results from cooperative action of the germination stimulators, alanine, mannitol and xylitol, and the natural antimicrobial substances serving as surfactants, bornyl acetate and geranyl acetate. When the early events of spore germination are triggered by the germination stimulators, fractures are formed on the surface of the spore coat layer. Then, the natural antimicrobial substances serving as surfactants, bornyl acetate and geranyl acetate, penetrate into the spore through the formed fractures and damage the components and structure of the spore cortex and core, eventually leading to the death of the spore. This spore-killing effect is more effective than is the use of the hexane extract alone. That is, the organic solvent extract of Torilidis Fructus, preferably the ethanol extract, has an excellent spore-sterilizing effect 100 times higher than conventional antimicrobial materials, which have a spore-sterilizing effect of about $10^1$, through both a direct sterilization mechanism mediated by the bornyl acetate and geranyl acetate ingredients, providing a sterilization effect of about $10^1$, and an indirect sterilization mechanism mediated by the germination inducers including alanine, mannitol and xylitol, providing a sterilization effect of about $10^2$. In addition, since the Torilidis Fructus extract of the present invention allows spore sterilization at low temperature with no heat treatment in food processing, it does not cause nutrient destruction or quality deterioration.

In another aspect, the present invention relates to a method of sterilizing spores of spore-forming microorganisms, which is based on treating the spores with the composition.

The composition is used within an effective amount, but the treatment method is not specifically limited.

A better understanding of the present invention may be obtained through the following examples which are set forth to illustrate, but are not to be construed as the limit of the present invention.

EXAMPLE 1

Preparation of Plant Extracts

Referring to FIG. 2, Plant Extracts were Prepared from plant materials including Torilidis Fructus according to the following procedure.

Washing and Grinding

Plant materials including Torilidis Fructus were washed with pure water to remove contaminants present on the surface of the plant materials, such as dust and other impurities. The washed plant materials were then individually ground finely using a grinder, and water content of each ground product was measured.

Ethanol Extraction

75% edible ethanol was added to the powdered Torilidis Fructus and other powdered plant materials at a final concentration of 0.1%, and mixed with stirring at room temperature (25° C.) for 24 hrs.

Filtration

After the mixing with ethanol was completed, each plant material was passed through a Whatman paper No. 2. The remaining pellet was again subjected to the ethanol extraction step and then filtered. The primary and secondary filtrate were combined and used in the next step.

Concentration by Solvent Evaporation

To concentrate the combined filtrates, the solvent was evaporated at 44° C. in a vacuum.

Freeze Drying

The vacuum-concentrated ethanol extract of Torilidis Fructus was freeze-dried to be provided in a paste state having a low water content, and was used for an antimicrobial test against vegetative cells and spores of spore-forming microorganisms.

Preparation of Hexane Extract

The ethanol extract of Torilidis Fructus was mixed with 100% hexane at room temperature (25° C.) for 24 hrs with stirring. The supernatant was recovered and used for an antimicrobial test against vegetative cells and spores of spore-forming microorganisms.

Preparation of Water Extract

Ethanol extracts of plant materials including Torilidis Fructus were individually mixed with water at room temperature (25° C.) for 24 hrs with stirring. The supernatants were recovered and used for an antimicrobial test against vegetative cells and spores of spore-forming microorganisms.

EXAMPLE 2

Preparation of *Bacillus* Spores

*Bacillus subtilis* spores were selected for use in an antimicrobial test against a spore-forming microorganism. In particular, *Bacillus subtilis* ATCC 6633 was used, which is naturally and abundantly occurring in food products, such as thick soypaste mixed with red peppers, soy sauce, red pepper powder, spices, dried vegetables, and the like.

Vegetative cells of *Bacillus subtilis* ATCC 6633 were subcultured, streaked onto tryptic soy agar (TSA) plates, and incubated at 30° C. for 48 hrs. The plates were then stored at a low temperature of 5° C. and used as a seed culture. After the seed culture was identified to have no morphological abnormality by microscopic observation, it was spread onto a nutrient agar plate containing magnesium sulfate (NAMS), and incubated at 30° C. for 48 hrs. After $10^{10}$-$\mathbf{10}^{12}$ spores had emerged, the plate was washed with physiological saline, and the spores were scratched with a platinum loop and transferred into a sterile tube. The spores were then centrifuged at 4° C. at 12,000 rpm for 2 min, and this centrifugation was carried out once more. After being microscopically observed to ensure the state of the spores, the pellet was subjected to on-off ultrasonication for 5 min to destroy only the vegetative cells, and was then centrifuged again. Spore formation was further confirmed by a Dorner method, and the spores were stored at −20° C. until use for an antimicrobial test.

EXAMPLE 3

Evaluation of Sterilization Effect of Torilidis Fructus Extract on Spores

To find natural substances having sterilization effects on spores, a total of 100 plant materials previously known to have antimicrobial activity was used, which consisted of 36 herbal spices including allspice, basil, black pepper, caraway, celery, cinnamon, cloves, coriander, cumin, fennel, and marjoram; 27 vegetables and tropical fruits including leeks, mugwort, red pepper, grossum green pimentos, watercresses, olives, radish sprouts, tomatoes, potatoes, gingers, green tea, grapes, golden kiwis, peaches, grapefruits, and lemons; 37 herbal materials used in traditional Chinese medicine, including forsythiae fructus, angelicae gigantis radix, chaenomelis fructus, akebiae caulis, cimicifugae rhizome, lonicerae flos, coptidis rhizoma, and torilidis fructus. The antimicrobial plant materials were extracted with 75% ethanol, concentrated in a vacuum, and freeze-dried to provide aqueous or powdered antimicrobial materials. Then, the ethanol extracts were screened to fine antimicrobial plant materials effective in the sterilization of spores and vegetative cells of spore-forming microorganisms. An antimicrobial test against spores of *Bacillus subtilis*, the representative spore-forming microorganism, was performed by optical density analysis at 600 nm and by counting of the total number of viable cells grown on a nutrient agar plate.

Optical density analysis is a method of indirectly analyzing the degree of growth of vegetative cells and spores by measuring OD values at 600 nm for vegetative cells and spores cultured in tryptic soy broth (TSB) at 37° C. for 18 hrs. The plant materials were primarily screened for candidates considered effective in sterilization by optical density analysis. Then, the candidates were further assessed for their antimicrobial effects by viable cell count. In detail, a spore suspension was mixed with physiological saline and a natural antimicrobial material (1% final concentration). The mixture was agitated at 30° C. for 3 hrs, and was then centrifuged at 12,000 rpm. After the supernatant, considered to contain the added antimicrobial material, was discarded, the pellet remaining in an Ependorf tube was covered with distilled water and centrifuged again to eliminate residual antimicrobial material. This washing step was repeated three times to obtain only spores treated with a natural antimicrobial material. This was done to evaluate the sterilization effects of the natural antimicrobial materials on pure spore samples. If the antimicrobial substances were not completely removed, residual antimicrobial substances may display their sterilization effects against vegetative cells grown from spores upon total viable cell count, thereby making it difficult to evaluate precise sterilization effects against spores. In this regard, the antimicrobial materials were completely removed by washing with water, and the spore pellet was resuspended in 0.85% physiological saline, smeared onto TSA plates, and cultured at 37° C. for 24 hrs and 48 hrs. The total number of viable cells was then counted to determine the lethal effects of the natural antimicrobial materials on both spores and vegetative cells. In addition, the sterilization effect was also examined at various concentrations of the natural antimicrobial materials to determine optimal concentrations and vegetative cells and minimum growth-inhibitory concentrations (MICs), effective for killing spores.

Figure 1:
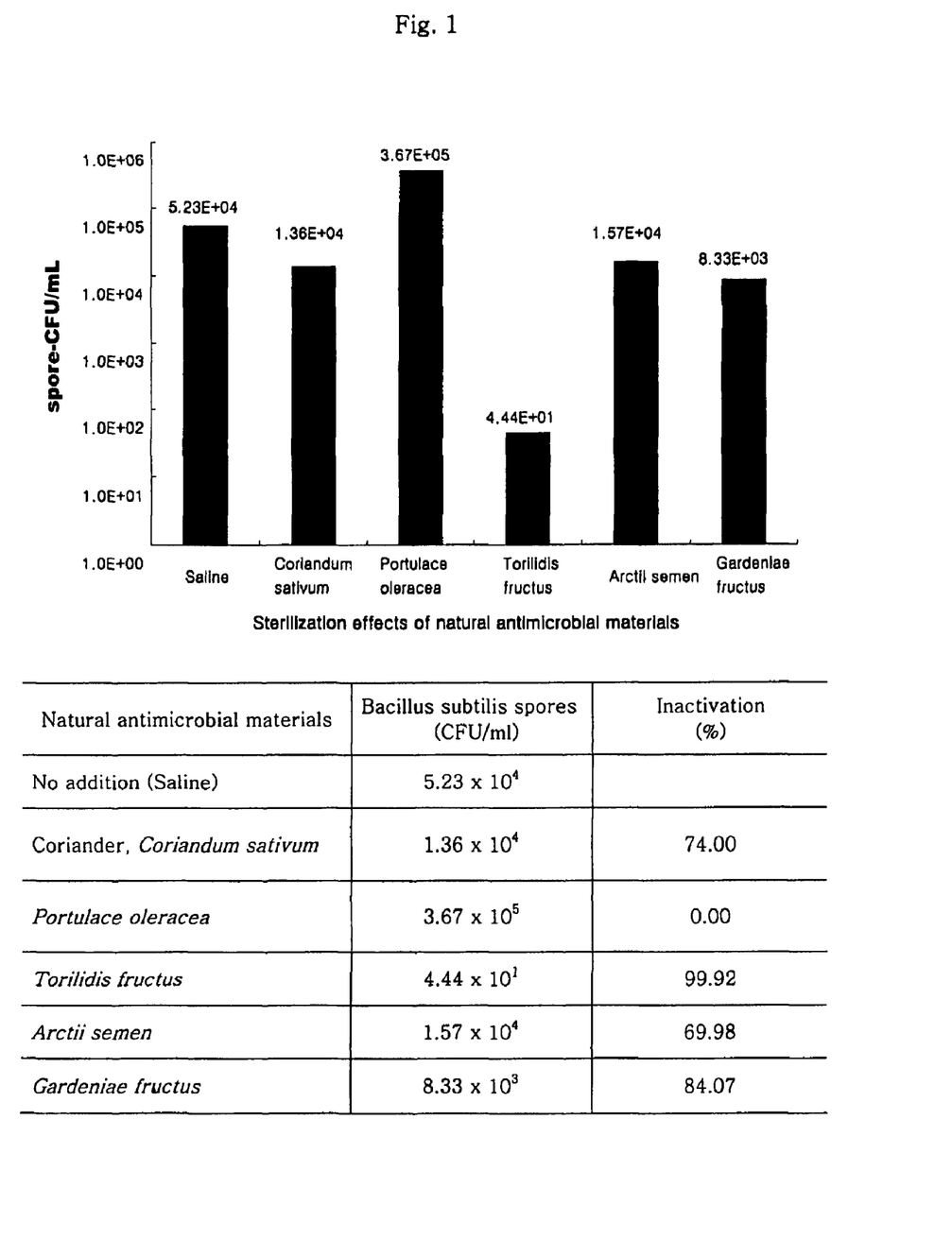
FIG. 1 shows the sterilizing effect an ethanol extract of Torilidis Fructus on spores of *Bacillus subtilis*.
Figure 2:
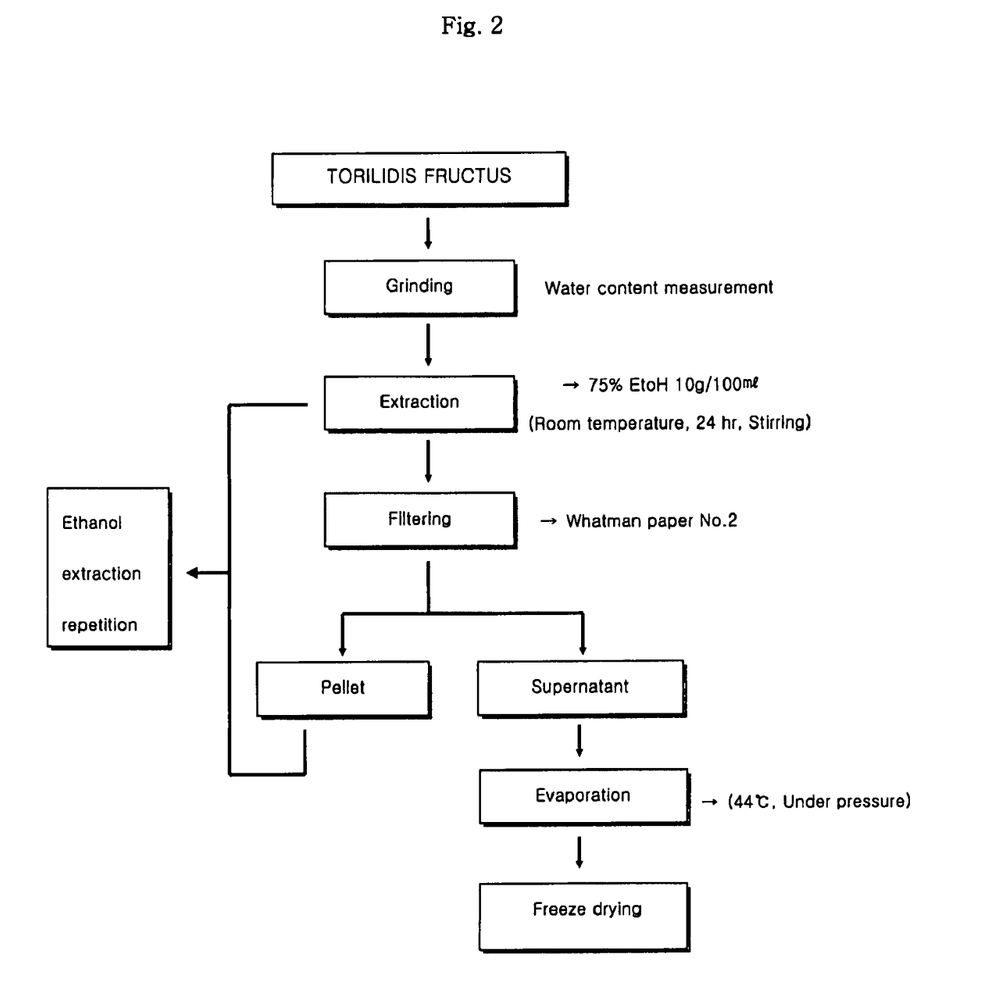
FIG. 2 shows a process for preparing an ethanol extract of Torilidis Fructus.

Each candidate antimicrobial material was added to a spore suspension in a 1% concentration relative to the spore suspension, incubated at 30° C. for 3 hrs, and assessed for sterilization and growth inhibitory effects. As a result, the ethanol extract of Torilidis Fructus was found to exhibit the highest sterilization effect of $10^3$ against vegetative cells and spores (FIG. 1). In addition to the ethanol extract of Torilidis Fructus, Chinese medical materials, Gardeniae Fructus and Arctii Semen, and an herbal spice, coriander (*Coriandum sativum*), displayed a sterilization effect of reducing spores of *Bacillus subtilis* by about $10^1$ CFU/ml. The 96 remaining plant materials were found to have no sterilization effect or poor sterilization effects in which the difference observed was not significant.

A search of related literature and patent publications resulted in the finding that the ethanol extract of the present invention has excellent sterilization effects of about 100 times or more compared to that of most natural antimicrobial materials, which have antimicrobial and growth inhibitory effects of about $10^1$.

EXAMPLE 4

Evaluation of Sterilization Effect of Torilidis Fructus on Spores According to Origin and Type In order to determine the sterilization effect of Torilidis Fructus on spores of *Bacillus subtilis* according to origin and type, *Torilis japonica* Decandolle and *Cnidium monnieri* (L.) Cussion, which were produced in both Korea and China, were treated according to the same method as in Example 1 and compared with each other with respect to sterilization effect. As a result, no large difference was observed between the different origins and types of Torilidis Fructus, which mostly displayed a sterilization effect of $10^2$ to $10^3$ on spores of *Bacillus subtilis*. Also, they all exhibited a similar yield of 10%. These results indicate that all types of Torilidis Fructus are useful for sterilizing spores.

EXAMPLE 5

Figure 3:
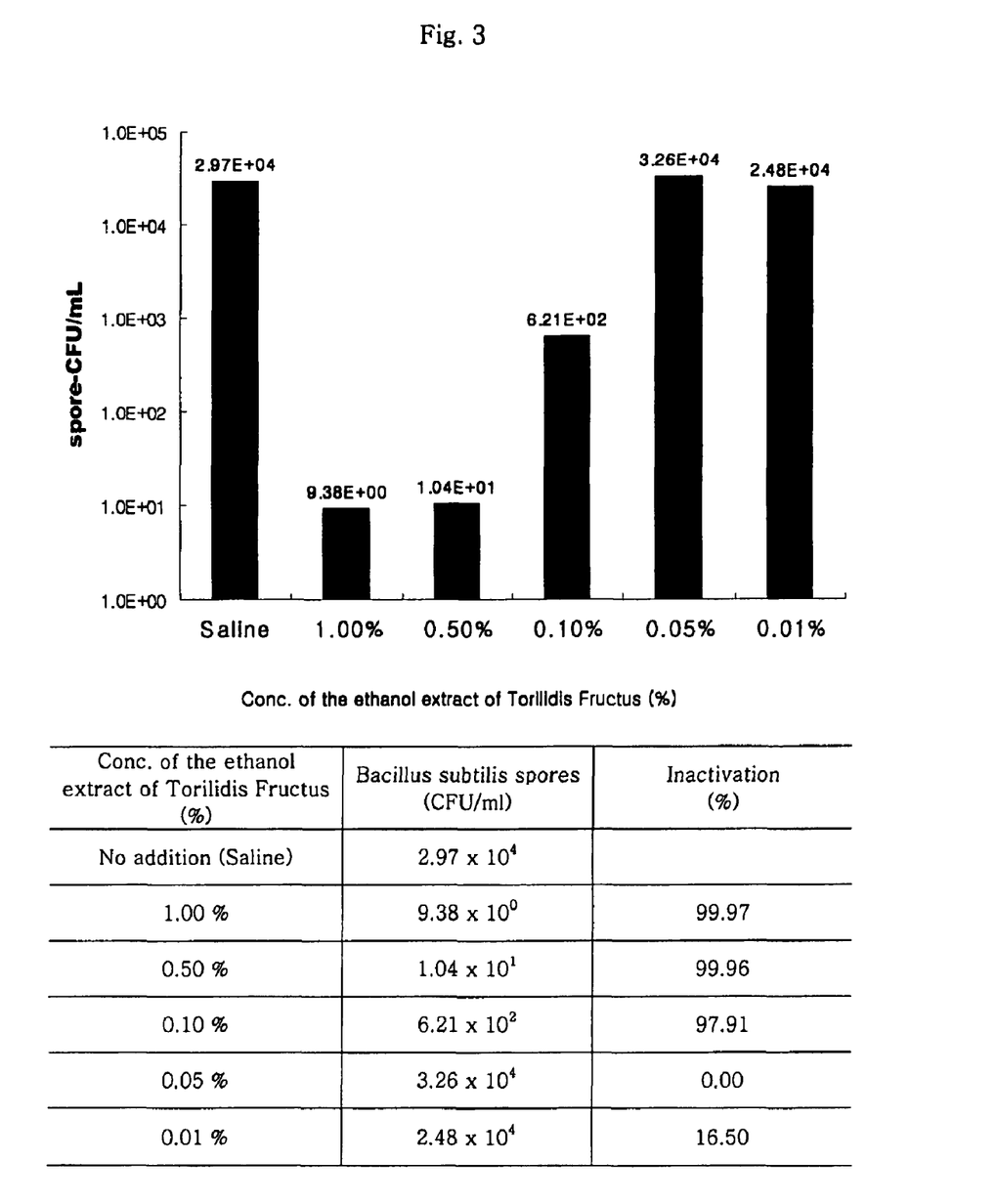
FIG. 3 shows the sterilization effect of an ethanol extract of Torilidis Fructus on spores of *Bacillus subtilis* depending on the concentrations.

Evaluation of Sterilization Effect of Torilidis Fructus Extract on Spores According to Concentration and Time To investigate the sterilization effect of the ethanol extract of Torilidis Fructus on spores of *Bacillus subtilis* according to concentration, the ethanol extract of Torilidis Fructus was added to a spore suspension in concentrations of 0.01%, 0.05%, 0.1%, 0.5% and 1.0% relative to the spore suspension. The ethanol extract of Torilidis Fructus exhibited a $10^2$ spore reduction (99% Inactivation) in a 0.1% concentration and a $10^3$-$10^4$ spore reduction (99.9-99.99% inactivation) in concentrations of 0.5% and 1.0%. The minimum growth-inhibitory concentration was found to be 0.1%, and 0.5% to 1.0% concentrations were considered optimal in consideration of sensory and economical factors including taste, production cost and selling price (FIG. 3).

Figure 4:
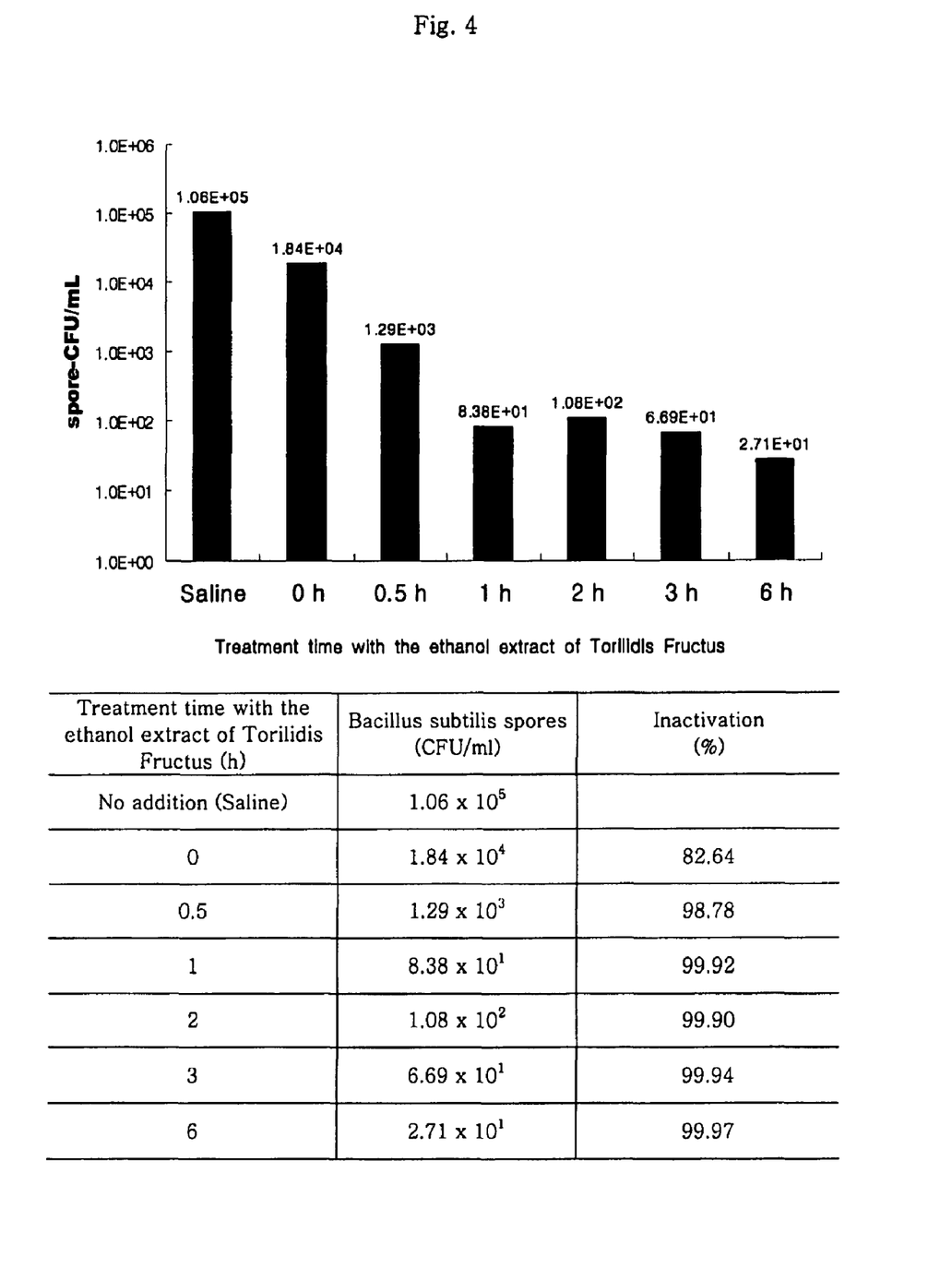
FIG. 4 shows the sterilization effect of an ethanol extract of Torilidis Fructus on spores of *Bacillus subtilis* over time.

To investigate the sterilization effect of the ethanol extract of Torilidis Fructus on spores of *Bacillus subtilis* over time, a spore suspension was treated with the ethanol extract of Torilidis Fructus, and sterilization effects were measured at given time points, 0.5 hr, 1 hr, 2 hrs, 3 hrs and 6 hrs. The ethanol extract of Torilidis Fructus displayed an effective sterilization effect of $10^2$ spore reduction (99% inactivation) after 30 min and the highest sterilization effect of $10^3$ to $10^4$ spore reduction (99.9-99.99% inactivation) after 1 hr. The excellent sterilization and growth inhibitory effects observed after about 1 hr of treatment, providing a $10^3$ or greater reduction in spores, result from the direct sterilization effect by antimicrobial substances and the indirect sterilization effect by germination stimulating substances (FIG. 4).

EXAMPLE 6

Evaluation of Sterilization Effect of Upper and Lower Phases of the Ethanol Extract of Torilidis Fructus on Spores The upper and lower phases of the ethanol extract of Torilidis Fructus were examined for their sterilization effects on spores of *Bacillus subtilis*. The lower phase was found to have almost no sterilization effect. In contrast, the upper phase exhibited a spore reduction of $10^2$, which was similar to that of the whole ethanol extract of Torilidis Fructus. These results indicate that the sterilization effect of the ethanol extract of Torilidis Fructus results from antimicrobial ingredients present in the upper phase.

EXAMPLE 7

Preparation of Hexane Extract from the Ethanol Extract of Torilidis Fructus

Figure 5:
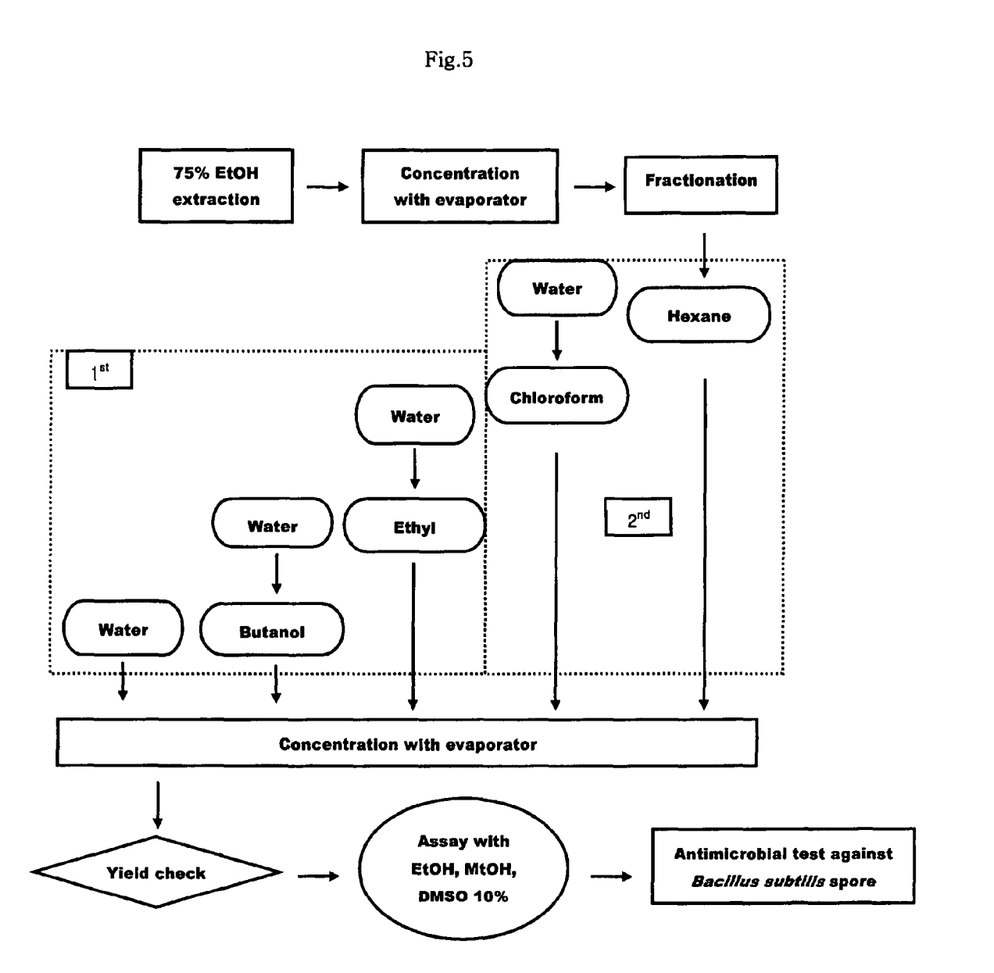
FIG. 5 shows a process for preparing a hexane extract and a water extract from an ethanol extract of Torilidis Fructus.
Figure 6:
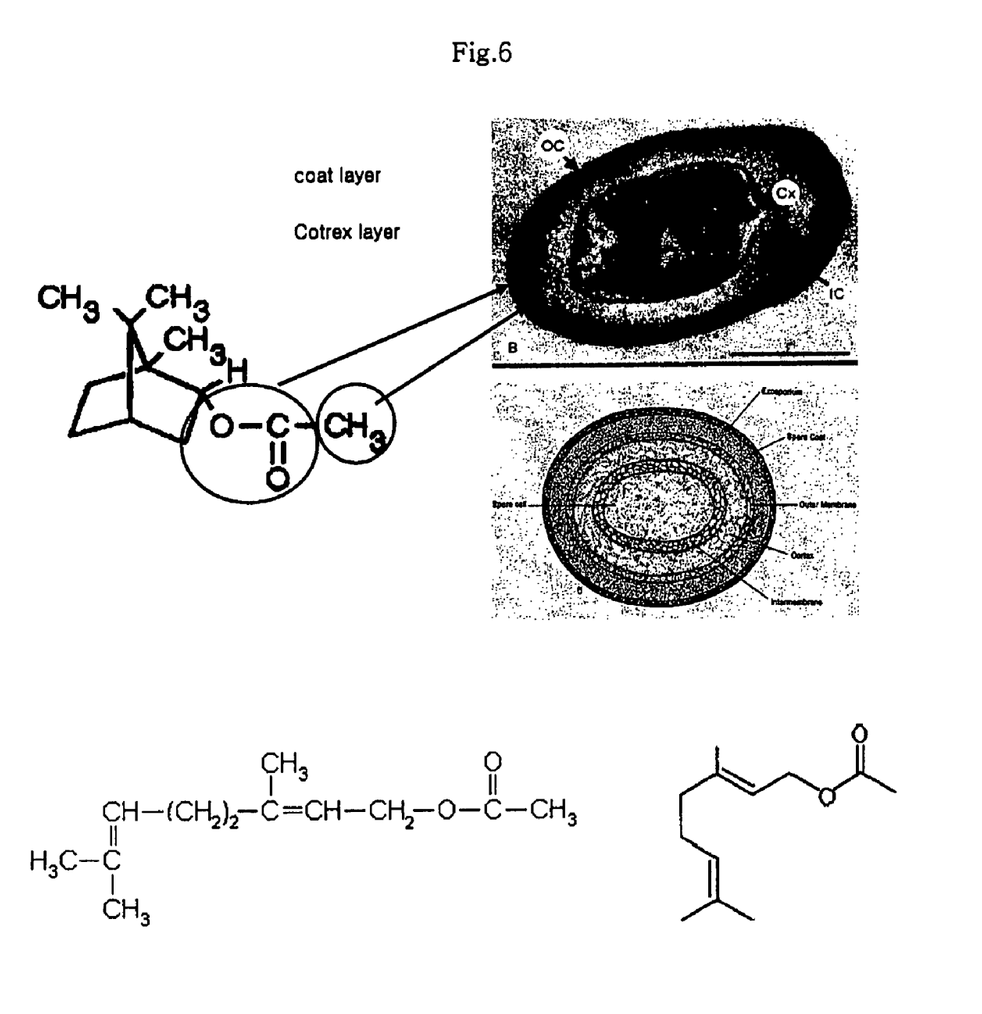
FIG. 6 shows the chemical structure and sterilization mechanism of bornyl acetate and geranyl acetate, which are major effective ingredients of an ethanol extract of Torilidis Fructus.

To determine the major ingredients responsible for antimicrobial activity against spore-forming microorganisms, the ethanol extract of Torilidis Fructus was extracted with hexane (FIG. 5). The literature search and analysis using laboratory equipment resulted in the finding that among hydrophobic group-containing antimicrobial ingredients extracted with hexane, including pinene, cymene, limonene, osthol, camphene, bornyl acetate and geranyl acetate, the bornyl acetate and geranyl acetate, which are able to serve as surfactants due to their structural property having both hydrophobic and hydrophilic groups, were major ingredients responsible for the antimicrobial activity of Torilidis Fructus against spore-forming microorganisms. FIG. 6 shows the chemical structure of the two ingredients.

EXAMPLE 8

Preparation of Water Extract from the Ethanol Extract of Torilidis Fructus

To examine the antimicrobial mechanism of the ethanol extract of Torilidis Fructus, the ethanol extract of Torilidis Fructus was extracted with water, and the water extract was analyzed for its ingredients.

Figure 7:
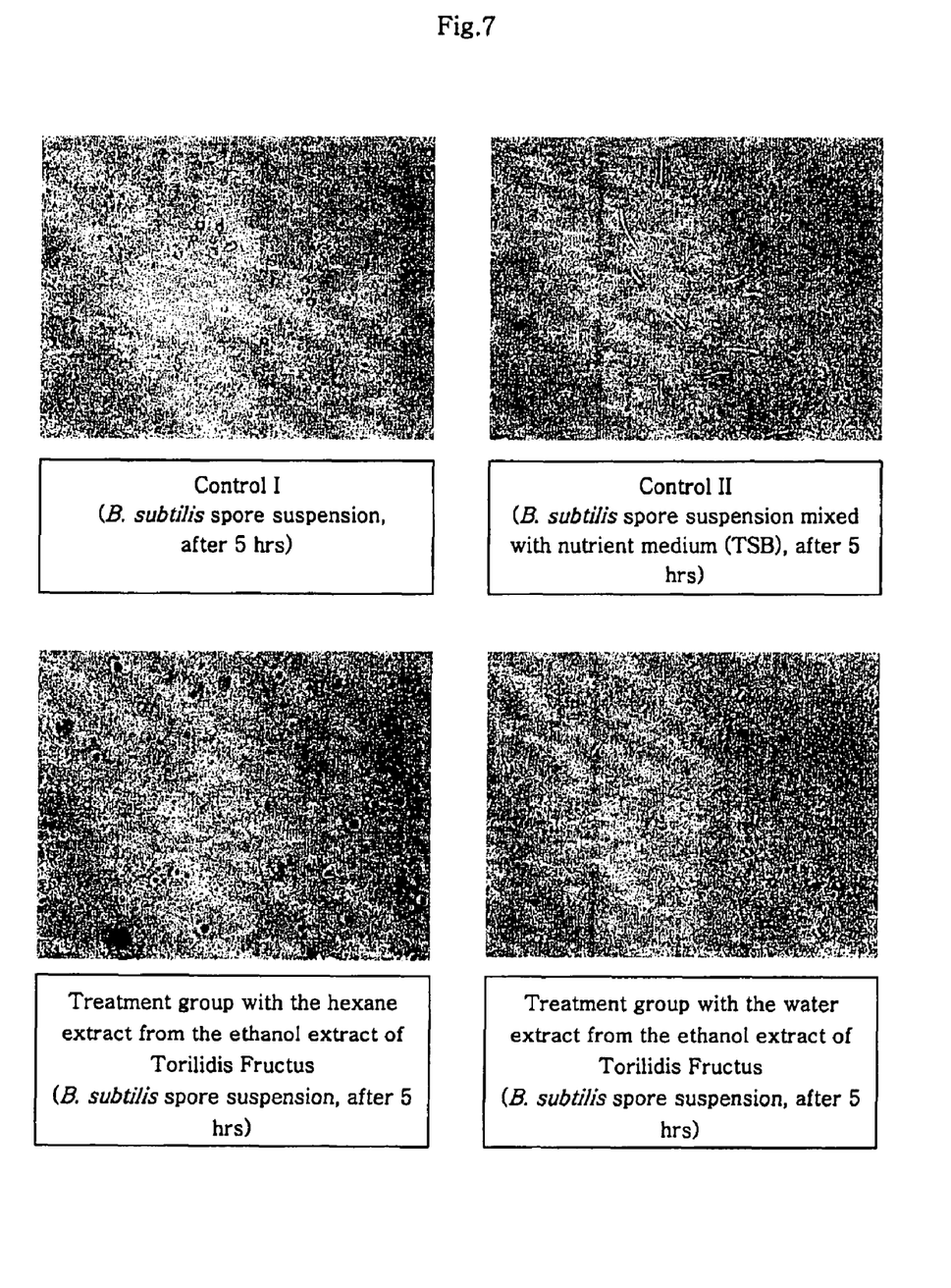
FIG. 7 shows microscopic observations of *Bacillus subtilis* spores, which were not treated with any extract, or were treated with a hexane extract or a water extract from an ethanol extract of Torilidis Fructus.
Figure 8:
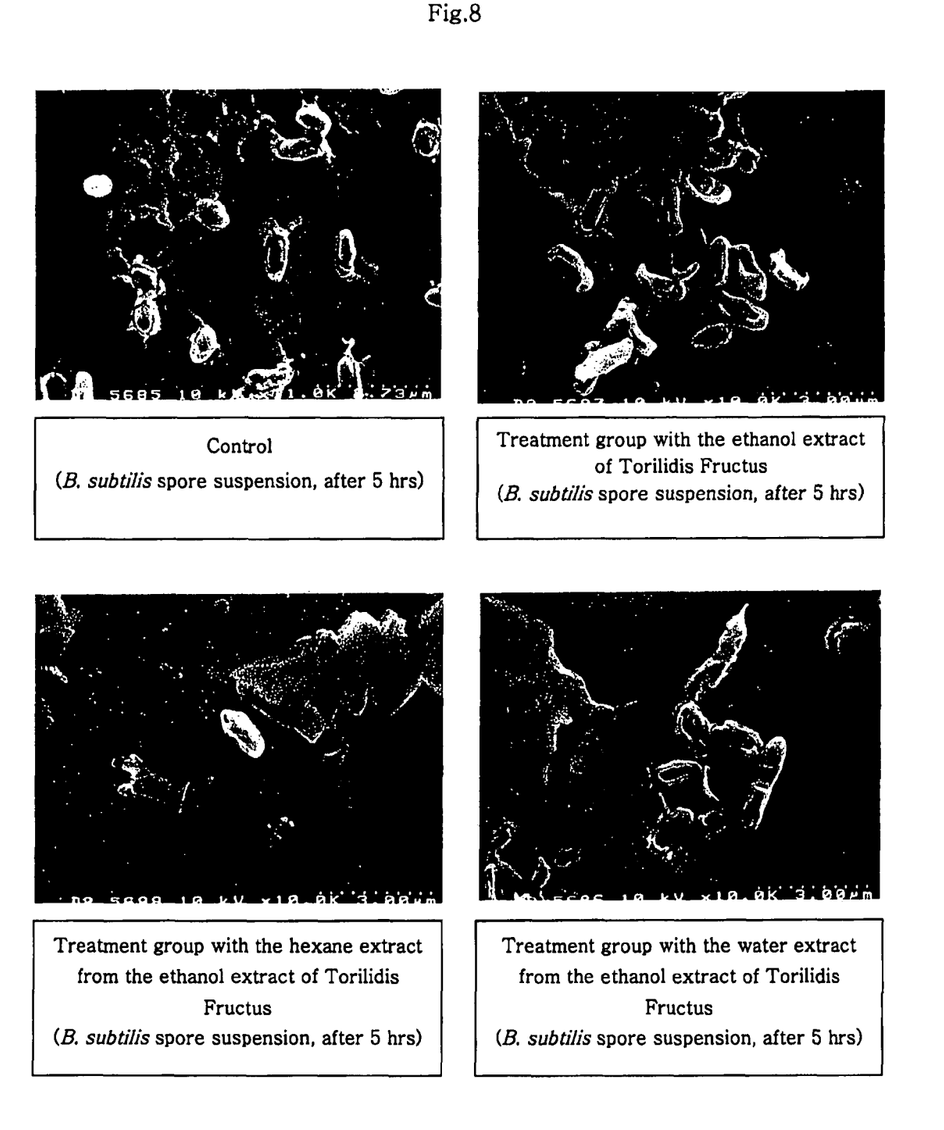
FIG. 8 shows microscopic observations of *Bacillus subtilis* spores, which were not treated with any extract, or were treated with an ethanol extract of Torilidis Fructus or a hexane extract or a water extract from the ethanol extract of Torilidis Fructus.

The water extract was subjected to ingredient analysis using a gas chromatograph-mass spectrometer (GC-MS). The water extract was found to contain large quantities of alanine, mannitol and xylitol, which are known as germination stimulators. These analysis results indicate that when *Bacillus subtilis* spores are treated with the water extract, the germination stimulators cause fracture damage to the coat layer, which is highly resistant to chemical antimicrobial substances by inducing spore germination, and the antimicrobial ingredients, serving as surfactants, of the ethanol extract of Torilidis Fructus, bornyl acetate and geranyl acetate, penetrate into the spore through the formed fractures, eventually destroying the spore core. FIG. 7 shows microscopic observations of *Bacillus subtilis* spores. The spores were not treated with any extract, or were treated with the hexane extract or water extract from the ethanol extract of Torilidis Fructus, at 30° C. for 3 hrs, and were microscopically observed after 5 hrs. When spores contained in a spore suspension were cultured in a nutrient medium (TSB), spores were found to germinate and grow into vegetative cells. When the spores were treated with the hexane extract, no germinated spores were observed, indicating that direct sterilization partially occurs due to the damage to the spore coat. When spores were treated with the water extract, the early events of spore germination were initiated by the germination stimulators. Since the early events of germination proceed by the water extract, the spores become less resistant to antimicrobial ingredients, and in this state, the effect of the antimicrobial ingredients of the hexane extract is doubled. FIG. 8 shows scanning electron microscopic observations of *Bacillus subtilis* spores, either treated with a Torilidis Fructus extract or not. When *Bacillus subtilis* spores were treated with the ethanol extract of Torilidis Fructus, the spore structure was destroyed, and the spore core was lost, indicating that spores were killed. The treatment of the hexane extract resulted in the partial damage to the spore coat. The treatment of the water extract resulted in structural changes to spores by induction of the early events of germination.

INDUSTRIAL APPLICABILITY

A composition for sterilizing spores and vegetative cells of spore-forming microorganisms comprising the organic solvent extract of Torilidis Fructus according to the present invention exhibits an excellent sterilization effect on both spores and vegetative cells of spore-forming microorganisms, and thus has various commercial applications as a natural sterilization material capable of effectively sterilizing spores at low temperature with no heat treatment.

The invention claimed is:

1. A method of sterilizing spores of the genus *Bacillus* or *Clostridium* comprising treating the spores with an effective amount of an organic solvent extract of Torilidis Fructus.

2. The method as set forth in claim 1, wherein said organic solvent extract is an alcohol extract.

3. The method as set forth in claim 1, wherein said organic solvent extract further comprises one or more ingredients selected from bornyl acetate and geranyl acetate following further extraction with hexane.

4. The method as set forth in claim 1, wherein said organic solvent extract comprises one or more ingredients selected from alanine, mannitol, and xylitol following further extraction with water.

* * * * *